US00PP32665P2

(12) United States Plant Patent
Gil

(10) Patent No.: US PP32,665 P2
(45) Date of Patent: Dec. 22, 2020

(54) ***CITRUS* TREE NAMED 'ONIX BLOOD'**

(50) Latin Name: *Citrus sinensis*
Varietal Denomination: Onix Blood

(71) Applicant: Agricola Ruiz Valero SL, Brenes (ES)

(72) Inventor: Juan Francisco Ruiz Gil, Seville (ES)

(73) Assignee: Agricola Ruiz Valero SL, Brenes (ES)

( * ) Notice: Subject to any disclaimer, the term of this patent is extended or adjusted under 35 U.S.C. 154(b) by 0 days.

(21) Appl. No.: 16/602,685

(22) Filed: Nov. 18, 2019

(51) Int. Cl.
*A01H 5/08* (2018.01)
*A01H 6/78* (2018.01)

(52) U.S. Cl.
USPC ..... Plt./202

(58) Field of Classification Search
USPC ..... Plt./201, 202
See application file for complete search history.

*Primary Examiner* — Susan McCormick Ewoldt
(74) *Attorney, Agent, or Firm* — Klarquist Sparkman, LLP

(57) ABSTRACT

A new variety of *Citrus sinensis* plant named 'Onix Blood', resulting from a spontaneous mutation, has fruit with a dark red-purple hue, almost black. About 60% of the 'Onix Blood' fruit display this characteristic. The remaining 40% of the fruit have 1 to 3 striking smooth chimeras, without bumps and vertically intense orange. The fruits of 'Onix Blood' are round-oval with a high red juice content that is balanced, have a juicy pulp, and are aromatic. These unique traits make it valuable blood orange tree.

7 Drawing Sheets

Botanical denomination: *Citrus sinensis.*
Variety designation: 'Onix Blood'.

BACKGROUND

The present invention is to a new and distinct variety of sweet orange tree which is named 'Onix Blood'. The new variety is a spontaneous genetic mutation of *Citrus sinensis* 'Sanguinelli' (unpatented). It was discovered in a *Citrus* field located in Carmona, Seville, Spain in 2012. The mutation was discovered in trees located within the field on planting lines. The plot is located in the fertile lowland in the Guadalquivir River that represents pseudogley soils. Soils in the area are mainly loose-textured or loose-textured to sandy. The climate is Mediterranean, with mild winters and. warm summers.

Asexual reproduction of the new *Citrus sinensis* 'Onix Blood' by vegetative reproduction (grafting) in Seville, Spain, has shown that the unique features of this new *Citrus* cultivar are stable and reproduce true to type in successive generations.

SUMMARY

The following traits have been repeatedly observed and represent the characteristics of the new cultivar 'Onix Blood'. The new cultivar 'Onix Blood' has not been observed under all possible environmental conditions. The phenotype may vary somewhat with variations in, for example, temperature, day-length, light intensity, soil types, and water and fertility levels without, however, any variance in genotype.

'Onix Blood' has a vigor and development similar to its mother tree in vegetative development. It has cramped growth habit and great productivity.

The most significant difference with respect to the 'Sanguinelli' variety is in the fruit and the bark. In the variety 'Sanguinelli', the bark has red areas on an orange background. In contrast, the bark of 'Onix Blood' is red-purple. In addition, the surface of the fruit of 'Onix Blood' is a dark red-purple hue, almost black. About 60% of the 'Onix Blood' fruit display this characteristic. The remaining 40% of the fruit have 1 to 3 striking smooth chimeras, without bumps and vertically intense orange. The fruits of 'Onix Blood' are round-oval with a high red juice content that is balance, juicy pulp, and aromatic. The new 'Onix Blood' variety has fruit with a larger diameter, higher anthocyanin content, so it has a greater color in the bark, as well as the characteristic orange chimera.

BRIEF DESCRIPTION OF THE DRAWINGS

The accompanying colored photographs illustrate the overall appearance and distinct characteristics of the new cultivar of *Citrus* 'Onix Blood'. The colors in the photographs are as close as possible with the photographic and printing technology utilized. The photographs are of 5 year old trees (measured from the time of grafting).

Certain characteristics of this variety, such as growth and color, may change with changing environmental conditions (e.g., light, temperature, moisture, nutrients availability, or other factors). Therefore, color characteristics of this new variety should be determined with reference to the observations described herein, rather than from the photograph alone.

DETAILED BOTANICAL DESCRIPTION

Figure 1:
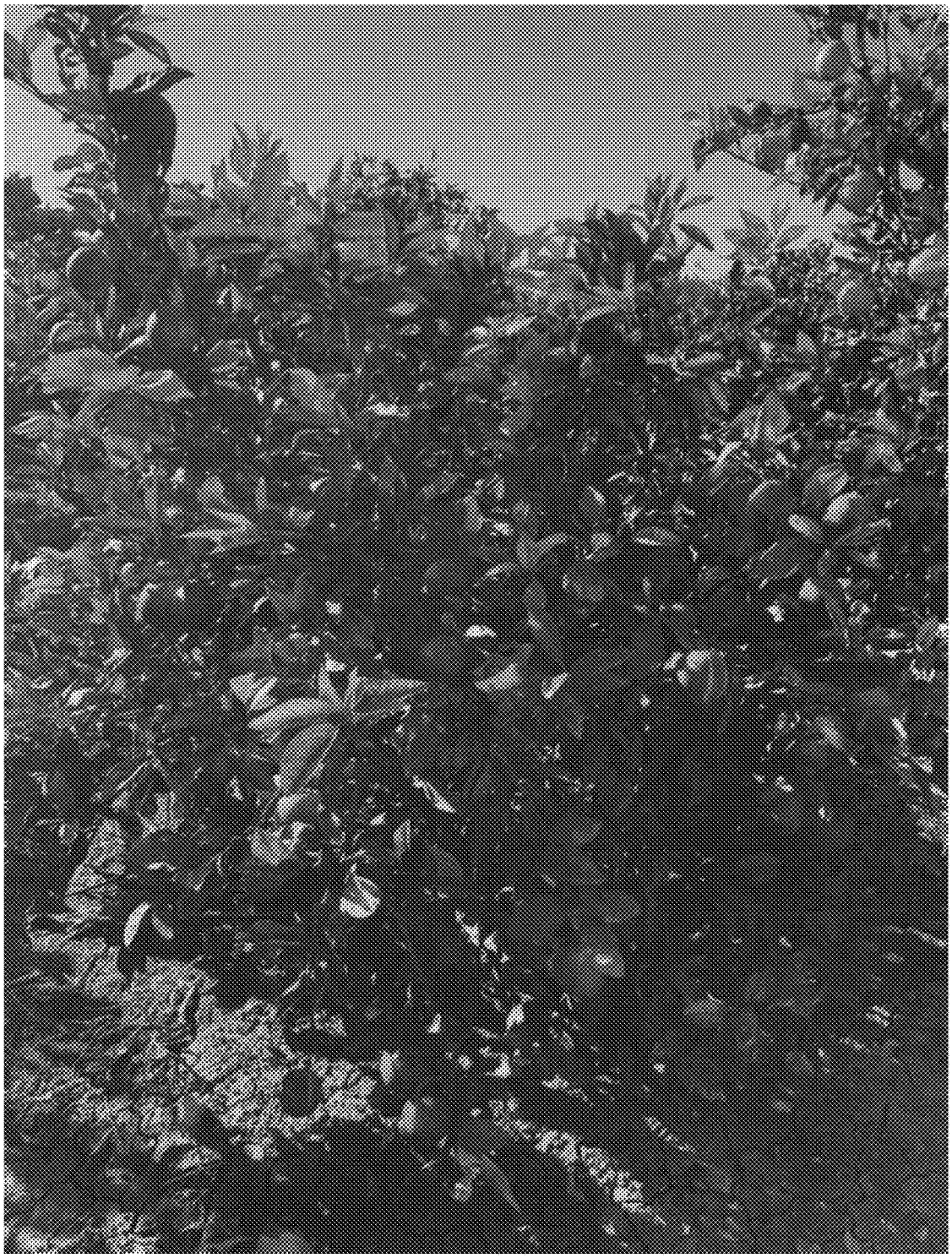
FIG. 1 shows a tree of 'Onix Blood' with fruit.
Figure 2:
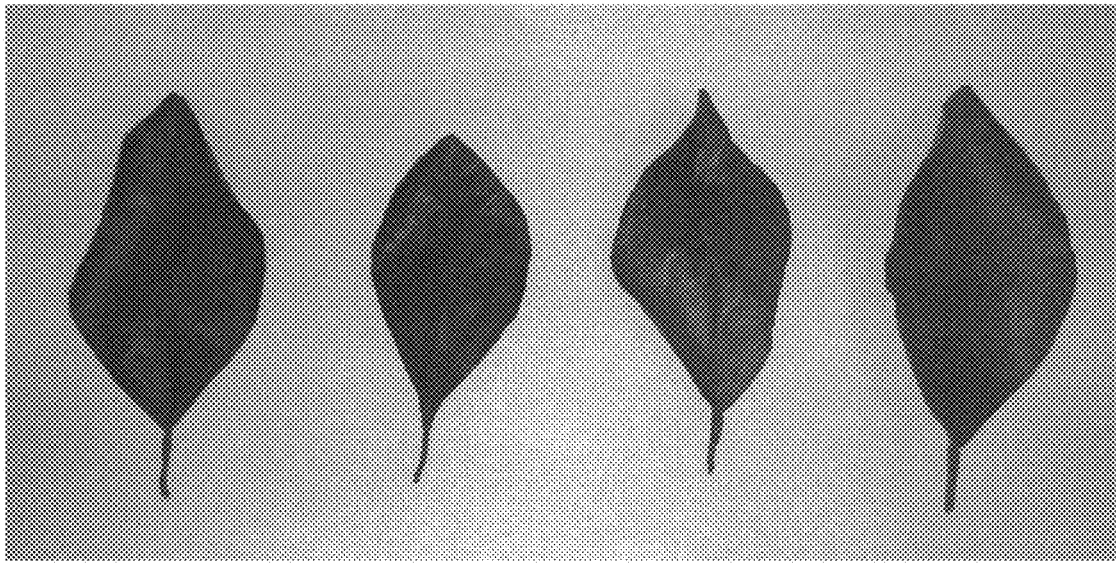
FIG. 2 show leaves of 'Onix Blood'.
Figure 3:
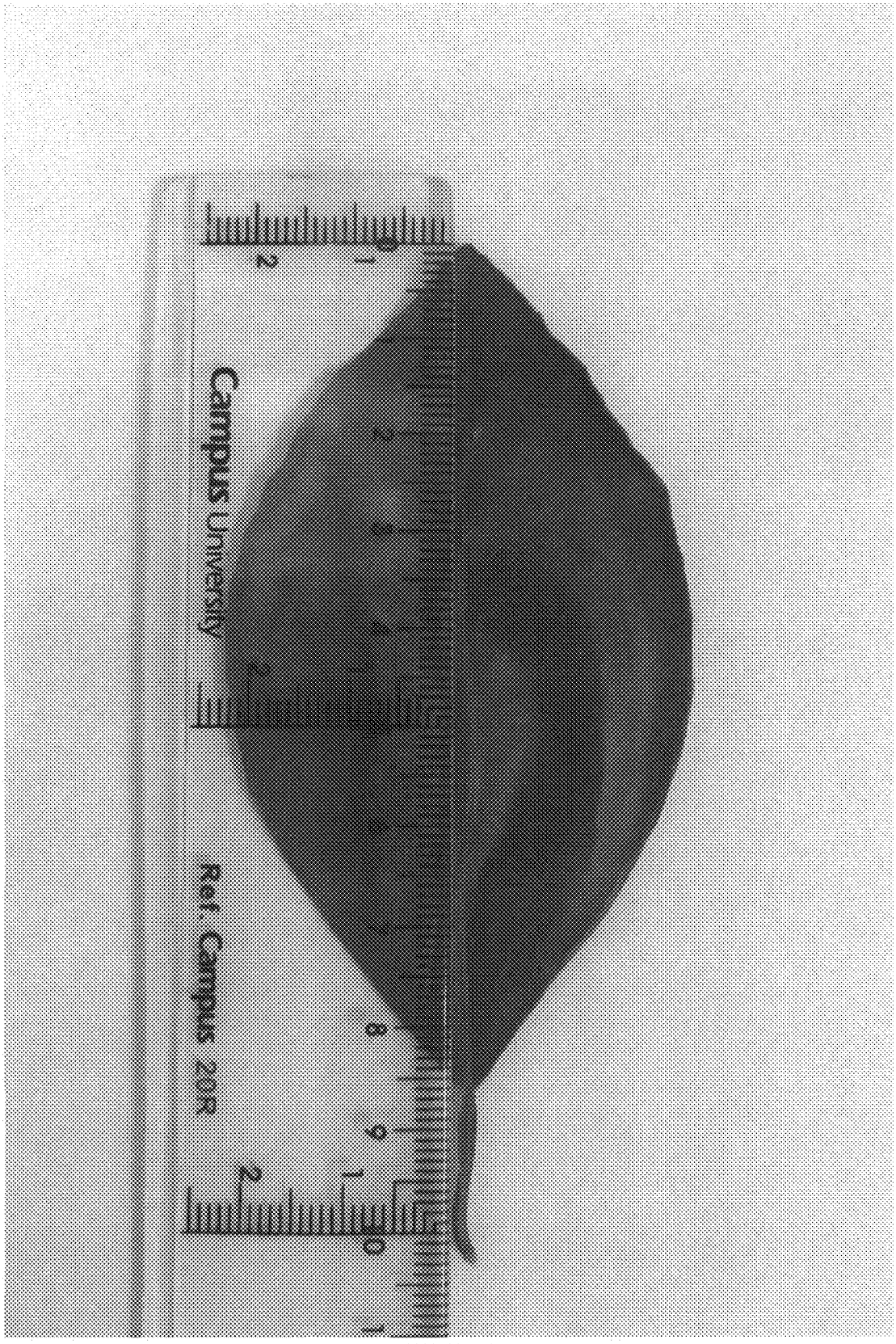
FIG. 3 shows leaf blade mean length (mm) of 'Onix Blood'.
Figure 4:
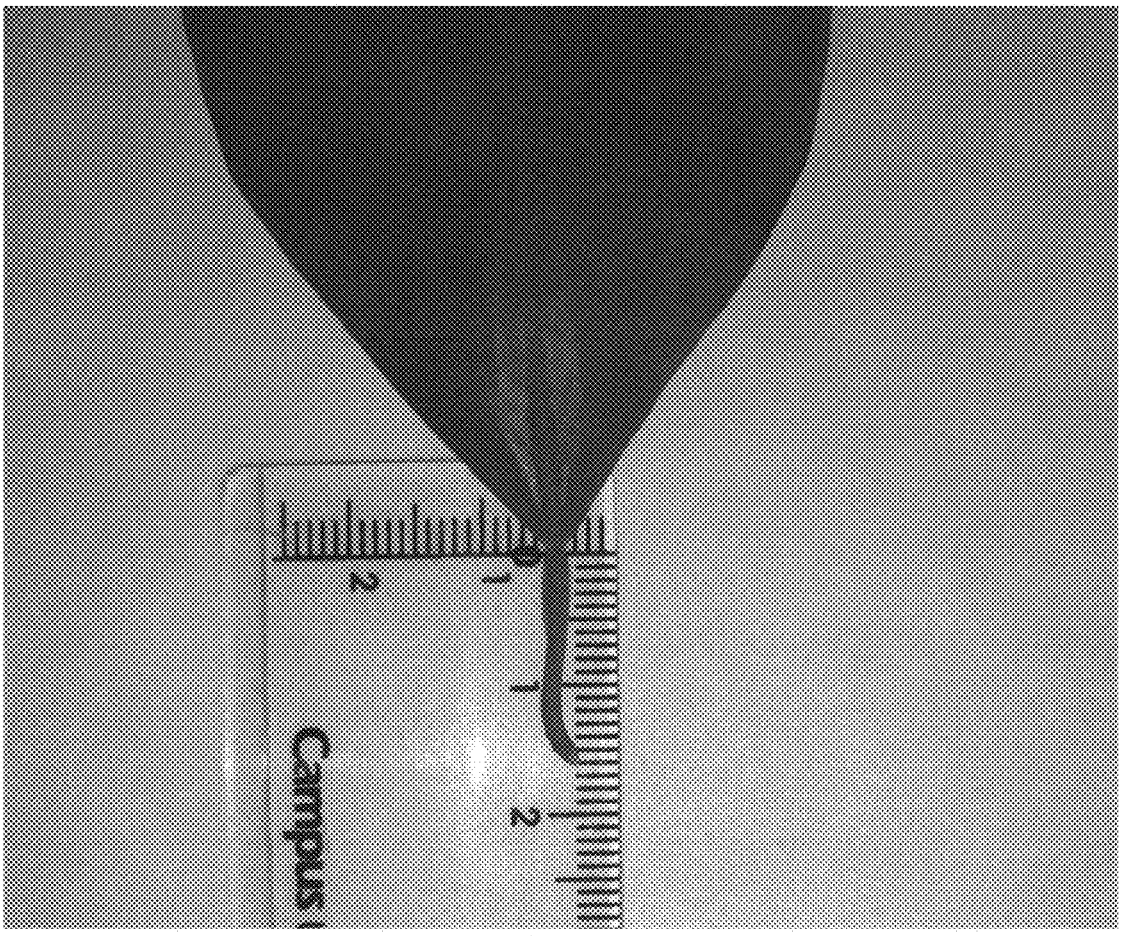
FIG. 4 shows leaf petiole mean length (mm) of 'Onix Blood'.
Figure 5:
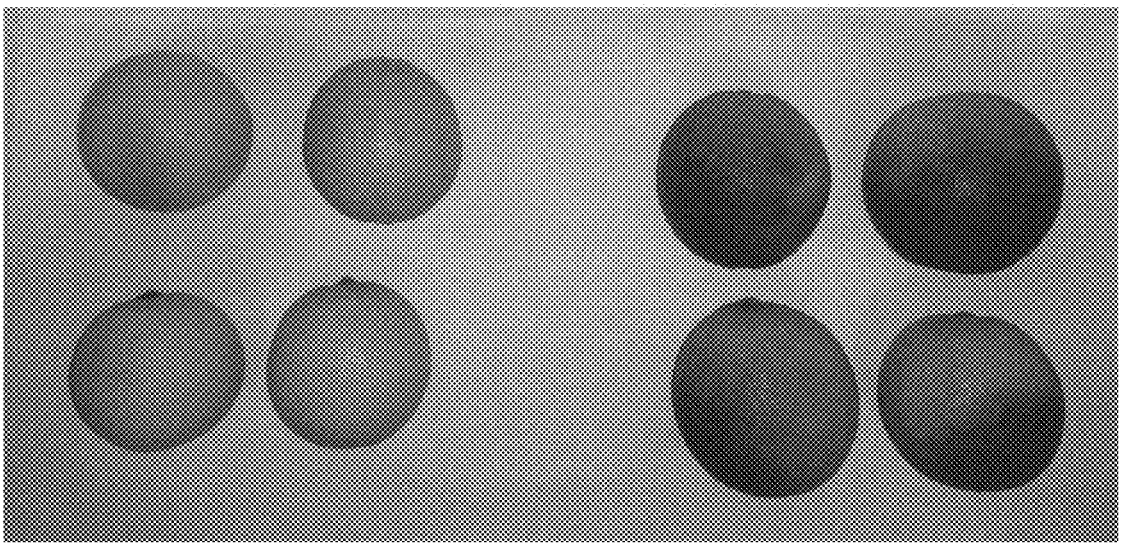
FIG. 5 shows the fruit rind (surface) color of 'Onix Blood' (right) and 'Sanguinelli' (left) mid-December 2019.
Figure 6:
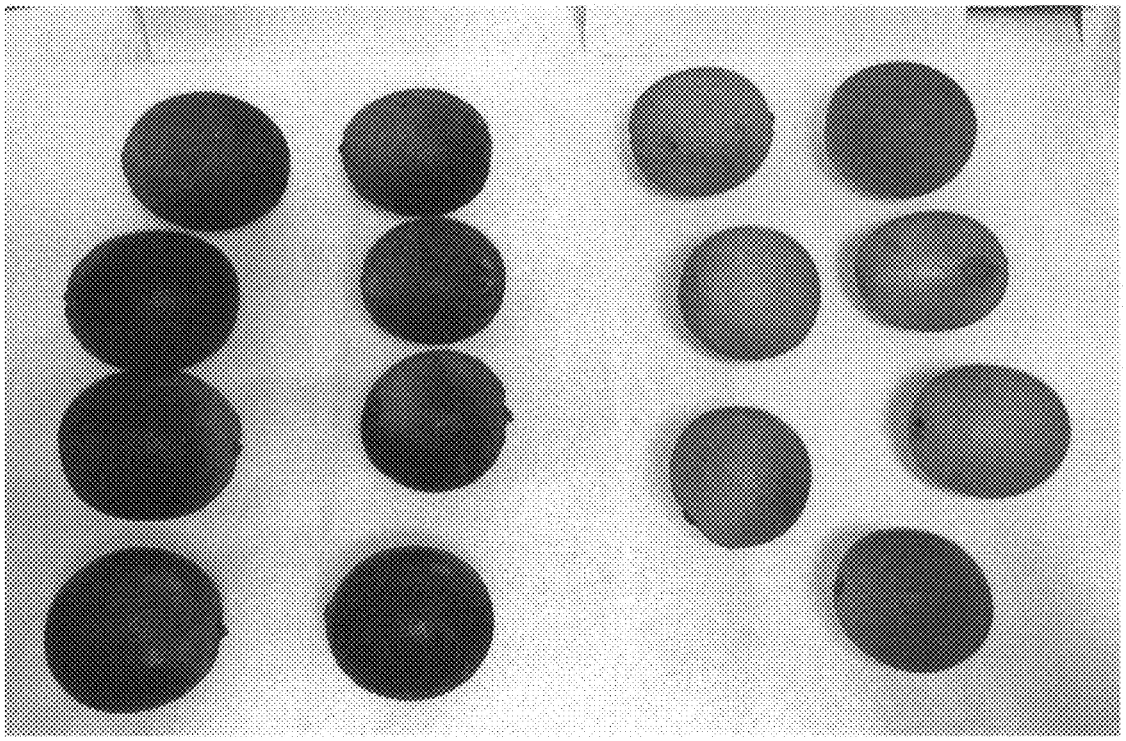
FIG. 6 shows the fruit rind (surface) color of 'Onix Blood' (left) and 'Sanguinelli' (right) mid-January 2020.
Figure 7:
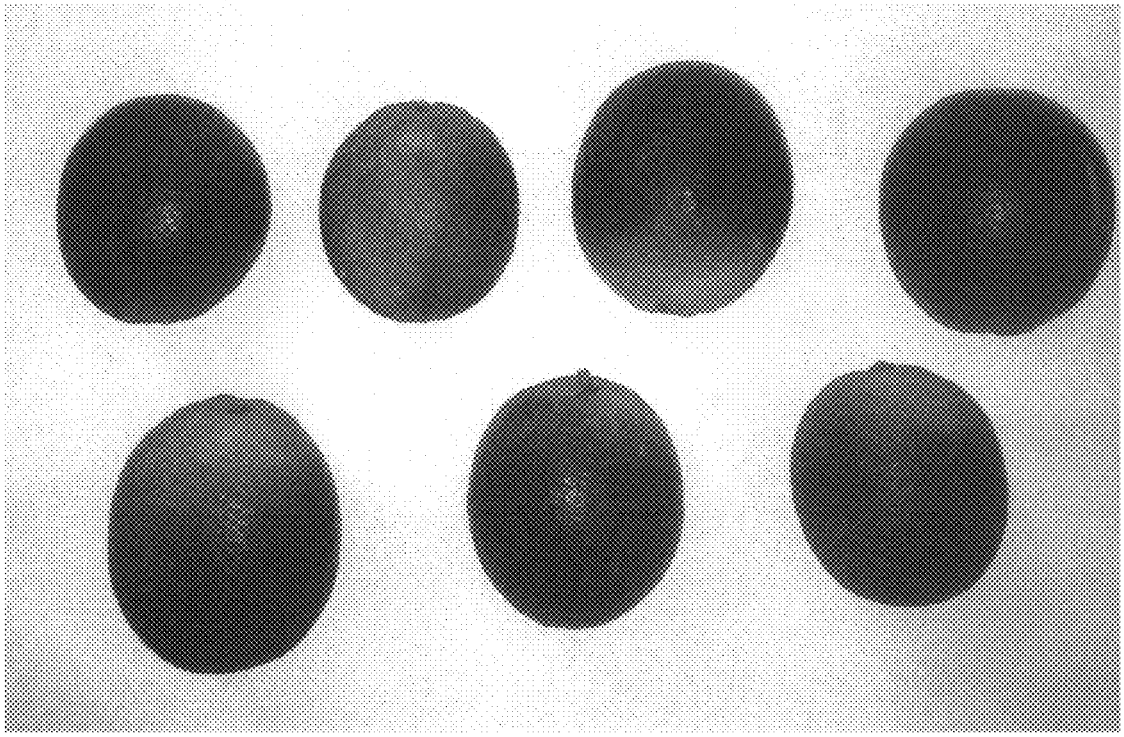
FIG. 7 shows the fruit rind (surface) color of 'Onix Blood' mid-February 2020.
Figure 8:
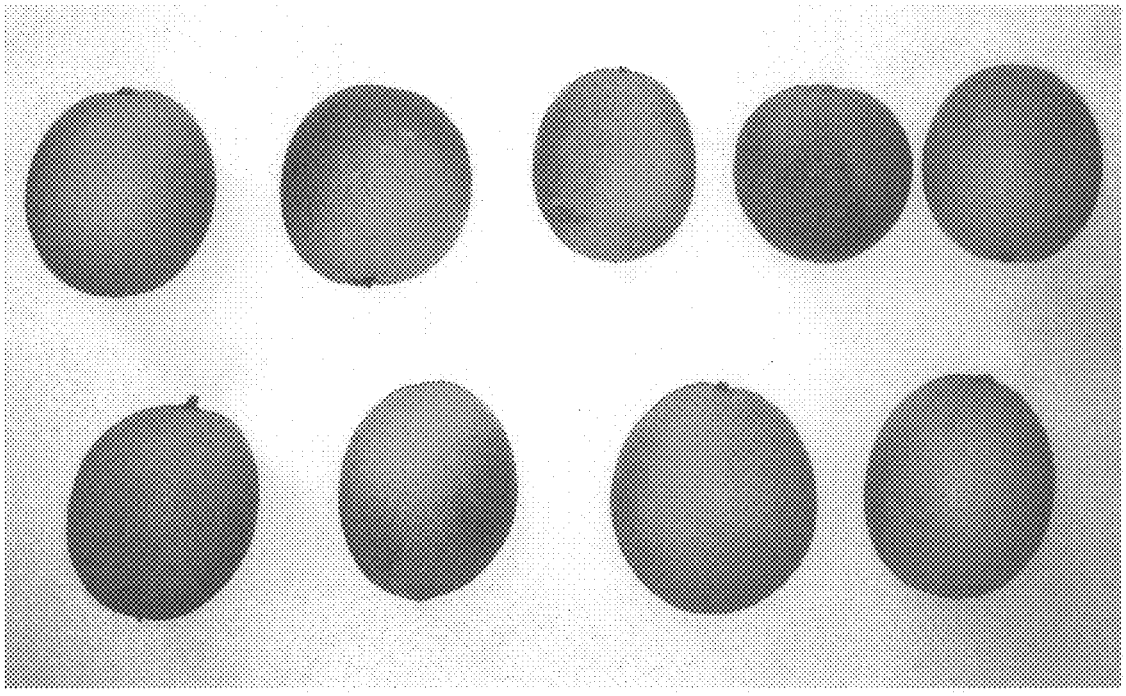
FIG. 8 shows the fruit rind (surface) color of 'Sanguinelli' mid-February 2020.

The described plants of the new cultivar were approximately 5 years of age, had been asexually reproduced by grafting and were observed growing outdoors in full sunlight in Seville, Spain. Observations obtained are described below.

All colors listed below are with reference to a Hunter Lab color space (strictly, Hunter L, a, b). The Hunter parameters "L", "a" and "b" represent the color luminosity and it is used to calculate the Color index (C.I.) according to Jiménez-Cuesta et al. (1981): C.I.=(a×1000)/(L×b), where "L" indicates lightness (L=0 yields black and L=100 indicates white) and "a" and "b" are the chromaticity coordinates ["a" indicate position between red and green (negative values indicate green while positive values indicate red) and "b" indicate position between yellow and blue (negative values indicate blue and positive values indicate yellow)].

The tree canopy volume (Vc) has been calculated by the formula of Turrel (1946): Vc ($cm^3$)=0,5238×(HT−HF)×$[(DT+DL)/2)]^2$.

For the classification of 'Onix Blood' leaves, the scales established by Carlton (1961) are used.

Observations obtained are described below:

Classification: *Citrus sinensis.*

Plant:

*Ploidy*.—Diploid.
*Self-incompatibility*.—Absent.
*Reproduction*.—Asexual (grafting).

Tree:

*Growth habit*.—Cramped.
*Density of spines*.—Absent or sparse.
*Total tree height* (*ht; cm*).—210.
*Tree low branches height* (*hf, cm*).—15.
*Cross section diameter* (*tree*) (*dt; cm*).—360.
*Longitudinal section diameter* (*tree*) (*dl; cm*).—330.
*Tree canopy volume* (*vc; cm*3).—22981.7.
*Trunk diameter of rootstock* (*dr; cm*).—16.
*Trunk diameter of cultivar* (*dc; cm*).—9.3.
*Ratio dr/dc*.—1.72.
*Trunk colour* (*hunter l, a, b*).—L: 24.85 a: 1.93 b: 8.65; IC: 8.979.
*Tree trunk texture*.—Smooth to slightly rough.
*Number of main branches*.—3.
*Average diameter of main branches* (*cm*).—7.5.
*Main branches color*. (*hunter l, a, b*).—L: 23.34 a: 1.39 b: 8; IC: 7.444.
*Main branches texture*.—Smooth to slightly rough.
*Root system*.—Formed by a pivoting root plus secondary roots and absorbent roots.

Leaf:

*Leaf arrangement*.—Alternate.
*Leaf blade color*.—"Discolora".
*Leaf adaxial blade green color* (*hunter l, a, b*).—L: 36.65 a: −9.01 b: 17.45; IC: −15.8.
*Leaf abaxial blade green color* (*hunter l, a, b*).—L: 45.75 a: −11.54 b: 20.55; IC: −12.4.
*Leaf base shape*.—Sharp or slightly rounded.
*Texture of leaf*.—Smooth.
*Venation pattern*.—"Pinnada" type "camptódroma".
*Leaf blade length* (*l*).—85.0 mm.
*Leaf blade width* (*m*).—50.0 mm.
*Leaf blade ratio* (*l/m*).—1.6. Leaf blade shape in cross section. Lanceolate.
*Leaf blade twisting*.—Absent.
*Leaf blade blistering*.—Absent.
*Leaf blade undulation of margin*.—Absent or weak.
*Leaf blade*.—Incisions of margin. Entire.
*Leaf blade*.—Shape of apex. sharp.
*Leaf blade*.—Emargination on top. absent.
*Petiole*.—Length is 15 mm; diameter is 17 mm.
*Petiole presence of wings*.—Absent.

Inflorescence:

*Flowering date*.—Early March.
*Flowering period*.—March-April (spring).
*Diameter of calyx*.—10 mm.
*Flower length of petal*.—17.0 mm.
*Flower width of petal*.—7.0 mm.
*Flower ratio length/width of petal*.—2.43.
*Flower length of stamens*.—15.0 mm.
*Flower basal union of stamens*.—Absent.
*Anther viable pollen*.—Present.
*Style length*.—19.0 mm.
*Style shape*.—Straight.

Figure 9:
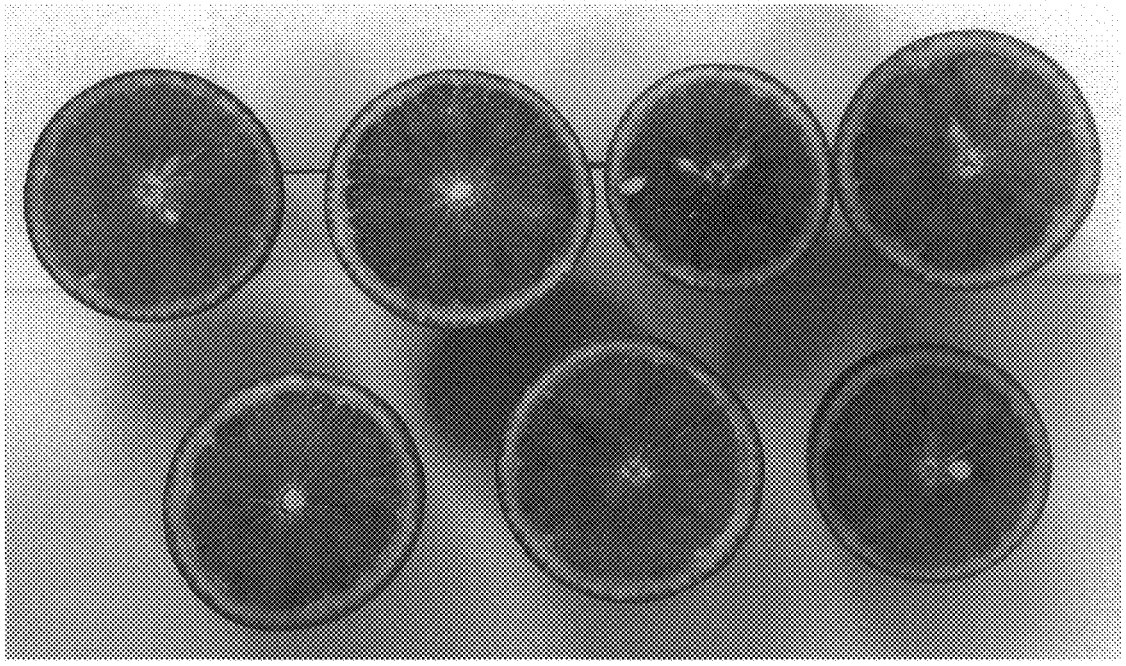
FIG. 9 shows the internal fruit color of 'Onix Blood'.
Figure 10:
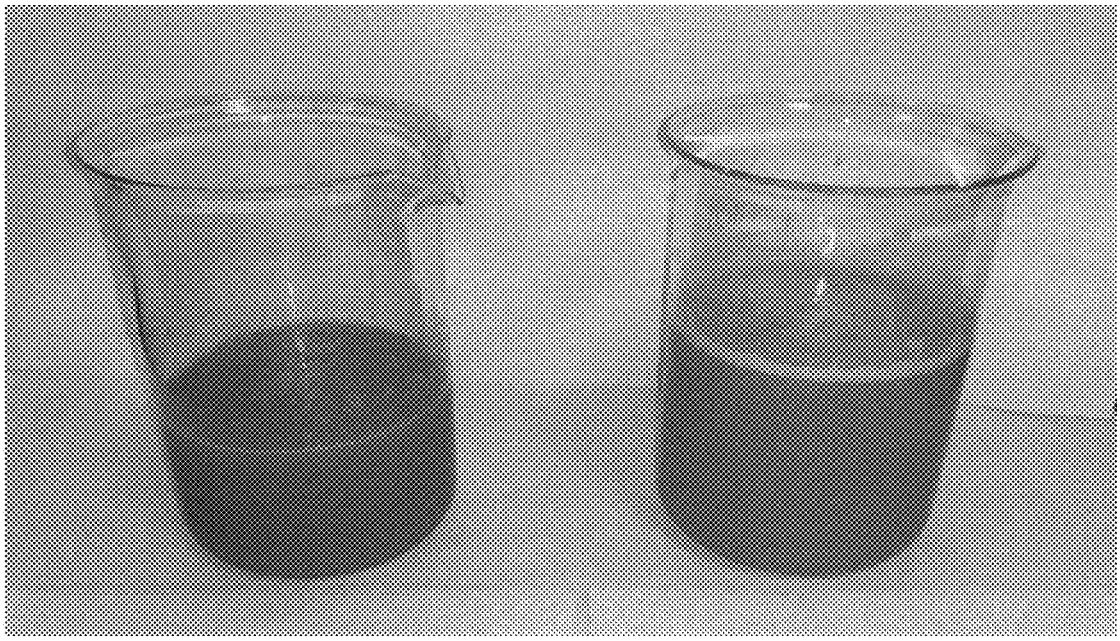
FIG. 10 shows the juice color of 'Onix Blood' (left) and 'Sanguinelli' (right) mid-January 2020.
Figure 11:
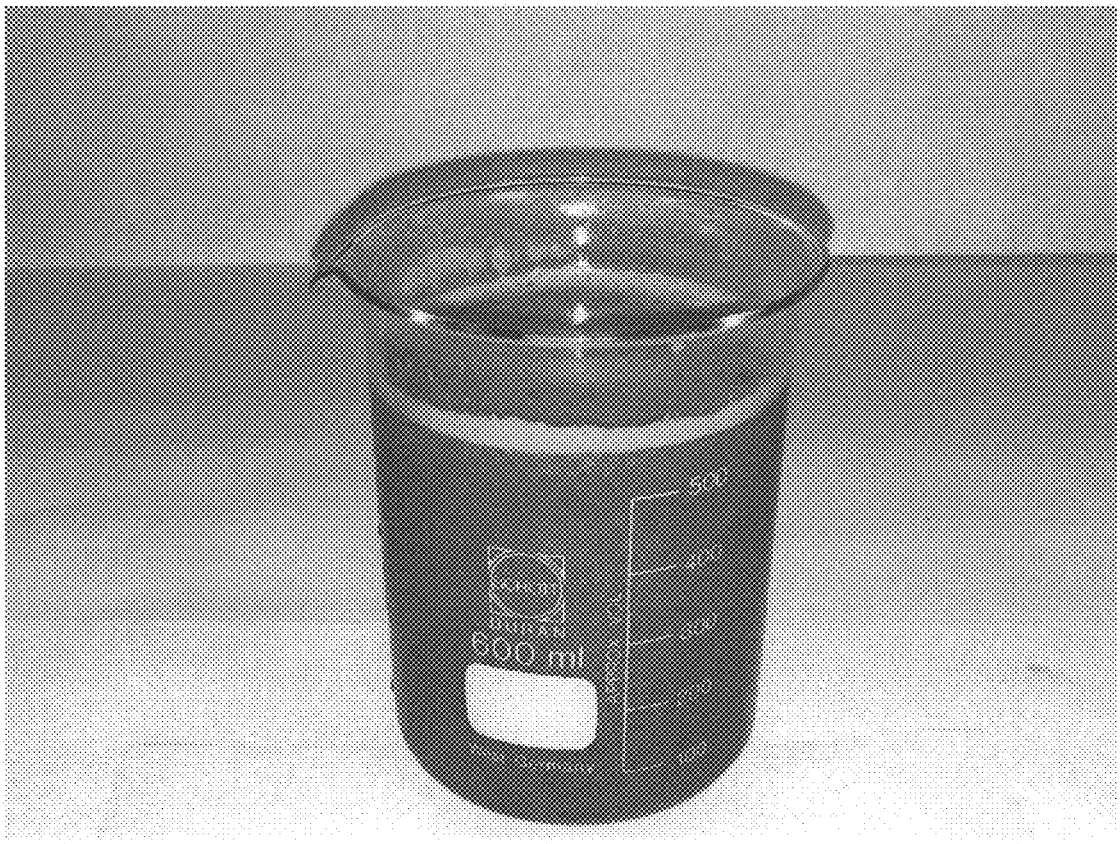
FIG. 11 shows the juice color of 'Onix Blood' mid-February 2020.

Fruit:

*Average diameter in february*.—69.0 mm.
*Average length in february*.—77.6 mm.
*Ratio diameter/length in february*.—0.89.
*Presence of narrowing at stalk end*.—Absent.
*Fruit rind* (*surface*) *color index* (*hunter l, a, b*).—L: 21.6 a: 11 b: 6.2; IC: 81.8.
*Fruit surface conspicuousness of larger oil glands*.—Scarce.
*Fruit surface presence of pitting and pebbling on oil glands*.—Absent.
*Fruit rind thickness in february* (*mm*).—5.1.
*Bicolored segments*.—Present (FIG. 9).
*Color of segments* (*hunter l, a, b*).—L: 46.94 a: 24.55 b: 27.32; IC: 19.136.
*Main color of flesh in december* (*hunter l, a, b*).—L: 26.36 a: 4.55 b: 10.42; IC: 18.7.
*Presence of rudimentary segments*.—Absent.
*Number of well-developed segments*.—11.5.
*Juice content in february* (%).—49.3.
*Juice*.—Density in February (g/cm3). 1.041.
*Juice*.—Total soluble solids in February (TSS; ° Brix). 11.7.
*Juice*.—Total acidity in February (TA; g/100cm3). 0.780.
*Fruit internal maturity index in february* (*tss/ta*).—15.0.
*Stockability*.—60-75 (under the following conditions: 4-5° C., relative humidity of 90% and concentration in CO2 between 0.20 a 0.25%).
*General shape of proximal part* (*excluding neck, collar and depression at stalk end*).—Flattened or strongly rounded.
*Presence of depression at stalk end*.—Absent.
*Presence of collar*.—Absent.

*General shape of distal part* (*excluding nipple, bulging of navel and depression at distal*).—Slightly rounded.

*Presence of depression at distal end*.—Absent.

*Presence of areola*.—Absent.

*Persistence of style*.—Present.

*Presence of navel opening*.—Absent.

*Presence of radial grooves at distal end*.—Absent.

*Fruit surface roughness*.—Smooth.

*Differently colored specks in flesh*.—Present.

*Bitterness of flesh*.—Absent.

*Filling of core*.—Medium density.

*Presence of navel* (*viewed internally*).—Absent.

*Seed surface*.—Smooth.

*Average number of seeds per fruit in february* (*self-pollination*).—0.9.

*Only varieties with seed*.—Polyembryony present.

*Time of maturity of fruit for consumption*.—From mid-January to the end of March, in Seville, Spain.

*Parthenocarpy*.—Present.

A comparison of observed characteristics of fruit from 'Onix Blood' and 'Sanguinelli' in December, January, February and April of the 2019/2020 season is shown below:

'Onix blood':

*Fruit weight* (*g*).—188.2 (December), 143.1 (January) and 194.3 (February).

*Fruit diameter* (*mm*).—69.9 (December), 61.2 (January) and 69.0 (February).

*Fruit length* (*mm*).—72.9 (December), 67.9 (January) and 77.6 (February).

*Ratio diameter/length*.—0.96 (December), 0.90 (January) and 0.89 (February).

*Peel thickness* (*mm*).—5.3 (December), 4.2 (January) and 5.1 (February).

*Fruit rind color index* (*ic hunter l, a, b*).—32.8 (December), 96.8 (January) and 81.7 (February).

*Number seeds per fruit*.—0.2 (December), 0.6 (January) and 0.3 (February).

*Juice*.—Average content (%): 48.4 (December), 51.1 (January) and 49.3 (February).

*Density* ($g/cm^3$).—1.032 (December), 1.044 (January) and 1.041 (February).

*Juice*.—Total Soluble Solids (TSS; ° Brix): 11.4 (December), 12.6 (January), 11.7 (February) and 13.0 (April).

*Juice*.—Total Acidity (TA; $g/100cm^3$): 0.526 (December), 0.543 (January), 0.780 (February) and 0.940 (April).

*Fruit internal maturity index* (*tss/ta*).—21.6 (December), 23.2 (January), 15.0 (February) and 13.8 (April).

'Sanguinelli':

*Fruit weight* (*g*).—139.9 (December), 130.9 (January) and 150.2 (February).

*Fruit diameter* (*mm*).—63.1 (December), 60,.6 (January) and 63.6 (February).

*Fruit length* (*mm*).—64.7 (December), 65.2 (January) and 72.2 (February).

*Ratio diameter/length*.—0.98 (December), 0,.93 (January) and 0.88 (February).

*Peel thickness* (*mm*).—5.3 (December), 4.5 (January) and 5.0 (February).

*Fruit rind color index* (*ic hunter l, a, b*).—11.2 (December), 32.0 (January) and 18.0 (February).

*Number seeds per fruit*.—0.2 (December), 0.4 (January) and 0.9 (February).

*Juice*.—Average content: 46.0 (December), 47.8 (January) and 45.3 (February).

*Juice*.—Density (g/cm3): 1.036 (December), 1.058 (January) and 1.044 (February).

*Juice*.—Total Soluble Solids (TSS; ° Brix): 11.6 (December), 12.5 (January) and 12.7 (February).

*Juice*.—Total Acidity (TA; g/100cm3): 0.438 (December), 0.577 (January) and 0.763 (February).

*Fruit internal maturity index* (*tss/ta*).—26.5 (December), 21.6 (January) and 16.6 (February).

I claim:

1. A new and distinct *Citrus* plant as herein illustrated and described.

* * * * *